United States Patent
Van Dijk et al.

(10) Patent No.: US 7,087,077 B1
(45) Date of Patent: Aug. 8, 2006

(54) BIOMEDICAL AID OR IMPLANT

(75) Inventors: Bastiaan Philip Van Dijk, Alkmaar (NL); Lucas Carolus Van Dijk, Rotterdam (NL)

(73) Assignees: Elephant Dental BV, Hoorn (NL); Academisch Ziekenhuis Rotterdam Dijkzigt, Rotterdam (NL)

( * ) Notice: Subject to any disclaimer, the term of this patent is extended or adjusted under 35 U.S.C. 154(b) by 0 days.

(21) Appl. No.: 09/958,656

(22) PCT Filed: Apr. 13, 2000

(86) PCT No.: PCT/NL00/00239

§ 371 (c)(1),
(2), (4) Date: Mar. 27, 2002

(87) PCT Pub. No.: WO00/61203

PCT Pub. Date: Oct. 19, 2000

(30) Foreign Application Priority Data

Apr. 13, 1999 (NL) ............................................. 1011779

(51) Int. Cl.
*A61F 2/06* (2006.01)

(52) U.S. Cl. ...................................... 623/1.15; 606/108
(58) Field of Classification Search ........................ None
See application file for complete search history.

(56) References Cited

U.S. PATENT DOCUMENTS 3,981,723 A * 9/1976 Tuccillo .................... 420/508
4,123,262 A * 10/1978 Cascone .................... 420/508
4,263,681 A    4/1981 Notton
5,630,840 A    5/1997 Mayer
5,645,558 A    7/1997 Horton
5,725,570 A    3/1998 Heath
5,733,326 A    3/1998 Tomonto et al.
5,895,401 A    4/1999 Daum et al.
5,911,731 A    6/1999 Pham et al.
6,027,528 A    2/2000 Tomonto et al.

FOREIGN PATENT DOCUMENTS

| | | |
|---|---|---|
| CA | 2041952 | 11/1991 |
| DE | 9320839 | 3/1995 |
| DE | 29518932 | 6/1996 |
| DE | 19531117 | 2/1997 |
| EP | 0455929 | 11/1991 |
| EP | 0743047 | 11/1996 |
| EP | 0809998 | 12/1997 |
| FR | 2392661 | 12/1978 |
| WO | 9319803 | 10/1993 |
| WO | 9530384 | 11/1995 |

* cited by examiner

*Primary Examiner*—Vy Bui
(74) *Attorney, Agent, or Firm*—Stevens, Davis, Miller & Mosher, LLP

(57) ABSTRACT

The invention relates to a stent manufactured from an alloy which contains at least 60% by weight, based on the weight of the alloy, of one or more metals selected from the group of gold, platinum, palladium and silver, silver being used only in combination with gold, platinum and/or palladium, and the alloy having a yield point of at least 200 $N/mm^2$ and an elongation at break of at least 8%.

8 Claims, No Drawings

BIOMEDICAL AID OR IMPLANT

This invention relates to a biomedical aid or implant. This invention relates in particular to biomedical aids such as stents, aneurysm clips, cardiac valves, occlusion coils, suture materials, artificial joints and osteosynthesis materials.

Stents are used in medicine inter alia for treating vascular stenoses and occlusions. In particular after Dotter treatments, stents are introduced into, often constricted or locally occluded, blood vessels to hold them open. Conventional areas of stent application are the coronary arteries in the heart, renal arteries, pelvic arteries and femoral arteries. Since a few years, stents have been used in combination with plastic (so-called stent-grafts) for the treatment of aneurysms, vascular occlusions or constrictions or arteriovenous fistulas.

A stent must satisfy a number of requirements. Important, first of all, are the mechanical properties. A stent is typically built up from thin wires or from a tube in which holes are provided, whilst the forces a stent is subject to in, for instance, an artery, can be considerable. Therefore it is important that the stent can resist sufficient pressure, but also that the stent is sufficiently elastic. Further, a stent must be made of biocompatible material, so as not to give rise to hypersensitivity phenomena or even rejection phenomena.

For intravascularly used stents, at present, with the growing importance of Magnetic Resonance Imaging (MRI), MR compatibility is important. The stents commercially available at present are manufactured from a metal alloy. The alloys used most are 'Stainless Steel 316' and Nitinol. Another material that is sometimes used is tantalum. Particularly Stainless Steel 316, the material used most because of its favorable mechanical properties, induces a local disturbance of the magnetic field used in MRI, to the extent that imaging the blood vessel adjacent the stent is seriously impeded. Although Nitinol and tantalum behave more favorably in MRI, their MR compatibility is not considered to be sufficiently good.

Accordingly, there is a need for an improved stent which has the favorable mechanical properties of the known stents, in particular of the stents manufactured of Stainless Steel 316, while at the same time exhibiting minor image artifact in MRI examination. Also, the new stent should be biocompatible.

Surprisingly, it has presently been found that the desired properties can be given to a stent by manufacturing it from a specific alloy based on one or more precious metals. Accordingly, the invention relates to a stent manufactured from an alloy which contains at least 60% by weight, based on the weight of the alloy, of one or more metals selected from the group of gold, platinum, palladium and silver, silver being used only in combination with gold, platinum and/or palladium, and the alloy having a yield point of at least 200 N/mm$^2$ and an elongation at break of at least 8%.

A stent manufactured from an alloy according to the invention has been found to yield significantly less disturbance of MRI images than does a stent manufactured from the materials conventionally used heretofore. In those cases where the more classic examination methods based on the use of X-rays are still employed, it is of advantage that the alloy of which the present stent is made further has a high radiopacity.

Further, the present stent possesses mechanical properties which are at least as good as those of the known stents. Furthermore, the alloy of which the present stent is manufactured has excellent wetting properties and can be processed in a very simple manner. By virtue of the favorable wetting properties, adhesion of substances from the environment takes place to a very minor extent only. It is to be noted here that, moreover, substantially no oxide film is formed on the surface of an object of the alloy, which is considered to be of advantage. Further, the present stent has a very good biocompatibility. It has been found that it is possible to make the stent nickel-free. Nickel is a material which is suspected to provoke allergic reactions in many people when used in vivo.

As stated, the alloy of which the present stent is manufactured is a precious metal alloy. At least 60% by weight, preferably at least 75% by weight, based on the weight of the alloy, consists of precious metal. In this connection, by the precious metals are meant the metals gold, platinum, palladium and silver. Of importance is further that silver is not the only precious metal in the alloy. If silver is present, at least one other element from the group of gold, platinum and palladium will be present in the alloy. Preferably, at least 5% by weight, more preferably at least 10% by weight, of gold, platinum and/or palladium is present. It has been found that when these conditions are met, an alloy is provided whose mechanical properties are sufficient for use in stents and other biomedical aids.

In a preferred embodiment, the alloy contains a combination of gold and palladium or a combination of silver and palladium. It has been found that through these combinations the alloy attains an optimum in magnetic properties and electrical conductivity. It has been found that to achieve good imaging in MRI, it is desirable that the alloy has a low magnetic susceptibility and a high electrical resistance.

When the alloy is based on a combination of gold and palladium, the relative weight ratio between gold and palladium will preferably be between 3:1 and 0.5:1, more preferably between 1.6:1 and 1:1. When the alloy is based on a combination of silver and palladium, the relative weight ratio between silver and palladium will preferably be between 3:1 and 0.3:1, more preferably between 1.3:1 and 0.4:1.

In addition to the precious metals referred to, the alloy preferably contains a number of dopes. The total amount of dopes is preferably between 0.5 and 40% by weight, more preferably between 4 and 40% by weight, depending on the amount of precious metal present. It is preferred that the alloy contains only metals, so that the total amount of dopes is preferably adjusted to the amount of precious metals present. Accordingly, in certain cases, the upper limit of the amount of dopes can be 25% by weight.

It will be clear that, though less desirable, the presence of very small amounts of impurities cannot be precluded. For instance, it does not constitute an insurmountable objection when very small amounts of silicon or carbon are present. These substances are preferably not present in amounts greater than 1.5% by weight for silicon and 1% by weight for carbon.

The dopes are preferably selected from the group of iridium, indium, gallium, tin, titanium, copper, zinc, and ruthenium. The dopes mentioned can be used both separately and in mutual combinations. It has been found that these dopes have a particularly favorable influence on the properties, in particular the mechanical properties, of the alloy. The dopes referred to are preferably present in the following amounts:

Iridium up to 30% by weight, more preferably from 0.1 to 10% by weight;

Indium up to 20% by weight, more preferably from 1 to 10% by weight;

Gallium up to 20% by weight, more preferably from 1 to 10% by weight;

Tin up to 20% by weight, more preferably from 1 to 10% by weight;

Titanium up to 40% by weight, preferably up to 15% by weight, more preferably from 0.5 to 5% by weight;

Copper up to 20% by weight, preferably up to 15% by weight, more preferably from 1 to 5% by weight;

Zinc up to 20% by weight, preferably up to 10% by weight, more preferably from 1 to 6% by weight; and Ruthenium up to 20% by weight, preferably up to 10% by weight, more preferably from 0.1 to 1% by weight.

By manufacturing a stent from an alloy which contains these amounts of dopes, excellent mechanical properties are combined with a very minor image artifact in MRI.

In addition to the dopes already mentioned, further, a metal can be present, selected from the group of rhodium, rhenium, cerium, germanium, boron, iron, tantalum, nickel, cobalt, aluminum, niobium, zirconium, manganese, chromium, molybdenum and tungsten. These metals too can be used both separately and in combinations. In particular when they are used in the amounts specified hereinafter, these dopes too can have a favorable effect on the alloy properties relevant to the invention. Nonetheless, the effect of these dopes will generally be somewhat less than that of the above-discussed dopes. The preferred amounts of this second group of dopes are:

Rhodium up to 30% by weight, preferably up to 10% by weight, more preferably from 0.1 to 1% by weight;

Rhenium up to 5% by weight, more preferably from 0.1 to 1% by weight;

Cerium up to 5% by weight, more preferably from 0.1 to 1% by weight;

Germanium up to 5% by weight, more preferably from 0.1 to 3% by weight;

Boron up to 3% by weight, more preferably from 0.1 to 0.5% by weight;

Iron up to 5% by weight, more preferably from 0.1 to 3% by weight;

Tantalum up to 5% by weight, more preferably from 0.1 to 2% by weight;

Nickel up to 30% by weight, more preferably from 1 to 10% by weight, still more preferably entirely absent;

Cobalt up to 30% by weight, more preferably from 1 to 10% by weight;

Aluminum up to 3% by weight, more preferably from 0.1 to 1% by weight;

Niobium up to 15% by weight, more preferably from 1 to 5% by weight;

Zirconium up to 5% by weight, more preferably from 0.1 to 2% by weight;

Manganese up to 5% by weight, more preferably from 0.1 to 2% by weight;

Chromium, molybdenum and tungsten jointly up to 5% by weight, more preferably from 0.1 to 1% by weight.

According to the invention, the alloy for manufacturing a stent must have a yield point of at least 200 N/mm² and an elongation at break of at least 8%. Preferably, the yield point is at least 300 N/mm² and the elongation at break is at least 20%. It has been found that through a suitable choice of the composition of the alloy, a yield point can be achieved of more than 400 N/mm² with an elongation at break of about 30%.

In the framework of the invention, the yield point is defined as measured according to ISO 6892 on an alloy which has been hard-annealed. The elongation at break is defined, according to the invention, as measured according to the same ISO 6892 on an alloy which has been soft-annealed. The conditions under which hard-annealing or soft-annealing occurred, are the optimum conditions for respectively hard- and soft-annealing the composition of the alloy. The artisan will be capable of choosing these on the basis of his ordinary skill in the art. For the measurement of the yield point and the elongation at break, a bar manufactured of the alloy to be measured is loaded incrementally on a tensile strength tester until break. The forces exerted on the bar are graphically represented and the elongation at break is determined by measuring the length of the parallel part of the bar before and after the test. More particularly, the following quantities can be calculated from the results of this test, in the following manner:

$$\text{tensile strength} = \frac{F_{max}}{A} \text{ N/mm}^2,$$

where $F_{max}$ is the highest tensile force applied (expressed in Newton) and A is the surface area of the cross section of the parallel part of the bar prior to break (expressed in mm²);

$$\text{yield point} = \frac{F_1}{A} \text{N/mm}^2,$$

where $F_1$ is the tensile force (expressed in Newton) at 0.2% permanent elongation; and $$\text{elongation at break} = \frac{L_1 - L_0}{L_0} * 100\%,$$

where $L_1$ is the length of the parallel part of the bar after the test, and $L_0$ is that same length before the test.

On the basis of his ordinary skill in the art, the artisan will be able to choose the composition of the alloy, in particular the nature and amount of the dopes present therein, such that the above-mentioned requirements regarding the mechanical properties are met.

The preparation of the alloy, which, incidentally, is known as such for, for instance, applications in dentistry, can be carried out as described in European patent application 0 598 431. Important here is that an alloy of a homogeneous composition is obtained.

The known preparation referred to comprises the steps of preparing a melt comprising the desired metals in the desired amounts, casting the melt to form an ingot, homogenizing by tempering, cooling and hardening. Tempering can be carried out at a temperature between 650 and 1200° C. Preferably, tempering is done at a temperature of about 900° C. Cooling is preferably carried out by cooling the tempered alloy in water. To obtain optimum properties, preferably, cooling is done fast (immediately after tempering). Preferably, the cooled alloy is subsequently rolled out to a smaller thickness or drawn into a wire. Rolling preferably occurs in different steps, alternated by a tempering at a temperature of 650–1200° C., preferably about 900° C. The eventual hardening of the alloy preferably occurs at a temperature of 400–700° C., more preferably at a temperature of 500–650° C.

Of the alloy, a stent can be formed in a conventional manner. According to the invention, the alloy can be used for manufacturing all known kinds of stents. Examples are stents for arterial applications, such as in the abdominal, pelvic, femoral, cervical, renal and coronary arteries, stents for venous applications, including applications in the venae cavae and application in TIPS (Transjugular Intrahepatic Portosystemic Shunt), stents of the balloon-expandable or self-expandable type, the group formed by covered stents, stent-grafts, and endografts (i.e. stents combined with vascular prosthetic material for treating aneurysmal and stenosing vascular disease including application in abdominal aortic aneurysm), and stents for non-vascular applications, such as hepatobiliary, gastrointestinal, urological and bronchial applications. For a description of examples of different stents, their form and applications, reference is made to Becker G. J., 'Vascular stents' and Dake M. D., 'Transluminal Placement of Endovascular Stent-Grafts for the Treatment of Thoracic Aortic Aneurysms', both from Abrams' Angiography, Ed. Baum S., Pentecost M. J., Little, Brown & Co., pp. 85–118 and 356–365, respectively, Boston 1997; and Hopkinson B. et al., 'Endovascular Surgery for Aortic Aneurysms', Saunders W. B., London 1997.

It has further been found that the alloy of which the present stent is manufactured is suitable for manufacturing other biomedical aids or implants. In the framework of the invention, the term 'biomedical aids or implants' is understood to include all objects foreign to the body, which are permanently or temporarily deployed in the body. Often, these objects serve to support or replace body functions which have failed wholly or partly, and/or to assist in restoring certain body functions or parts of the body. The aids/implants involved here are particularly those where in a comparable manner the mechanical properties and MRI properties play a role, and which are utilized in the human body at a site where they are not exposed to the atmosphere, which is in effect understood to include all applications not belonging to dentistry.

Accordingly, the invention further relates to the use of the above-described alloy for manufacturing such biomedical aids or implants. Examples of such aids/implants comprise aneurysm clips, cardiac valves, occlusion coils (for therapeutic occlusion of arteries, veins and aneurysms), suture materials, artificial joints and osteosynthesis materials, such as screws, pins and plates for the purpose of surgical reconstruction of bone structures.

For a description of examples, as well as the applications and possible forms of the aids mentioned, reference is made to Pollak J. S., White R. I., 'Mechanical Embolic Agents', Abrams' Angiography, Ed. Baum S., Pentecost M. J., Little, Brown & Co., pp. 55–79, Boston 1997 (occlusion coils); Yasargil, M. G., 'Microneurosurgery', George Thieme Verlag, pp. 212–213 and 245–271, New York 1984 (aneurysm clips); Kirlin J. W., Barratt-Boyes B. G., 'Cardiac Surgery', 2$^{nd}$ edition, vol. 1, ch. 11, pp. 474–476, Churchill Livingstone Inc., New York 1993 (cardiac valves and sutures); Muller M. E., Allgower M., Schneider R., Willenegger H., 'Manual of Osteosynthesis', Springer Verlag 1979 and Browner B. D., Edwards C. C., 'The Science and Practice of Intramedullary Nailing', Lea & Febiger 1987 (both bone screws, bone pins and bone plates); and Lemons J. E., 'Metallic Alloys' and Rand J. A. et al., 'Cemented Total Knee Arthroplasty', both from 'Joint Replacement Arthroplasty', Ed. Morrey B. F., Churchill Livingstone, pp. 13–22 and 1007–1021, respectively, New York 1991, and pp. 147–240, 275–329 and 419–436 from the same book (artificial joints).

In the above text and the following example, all percentages are by weight and based on the total weight of the alloy, unless specified otherwise.

EXAMPLE

Analogously to the procedure described in the Example of EP-A-0 598 431, the alloys were prepared with the following compositions:

| Alloy A: | Au | 0.1% by weight |
|---|---|---|
| | Pt | 0.5% by weight |
| | Pd | 60.6% by weight |
| | Ag | 28.0% by weight |
| | Sn | 7.3% by weight |
| | In | 2.0% by weight |
| | Ga | 1.2% by weight |
| | Zn | 0.2% by weight |
| | Ru | 0.1% by weight |
| Alloy B: | Au | 2.0% by weight |
| | Pd | 78.9% by weight |
| | Cu | 10.0% by weight |
| | Ga | 9.0% by weight |
| | Ir | 0.1% by weight |
| Alloy C: | Au | 52.0% by weight |
| | Pd | 38.0% by weight |
| | In | 8.2% by weight |
| | Ga | 1.6% by weight |
| | Ag | 0.1% by weight |
| | Re | 0.1% by weight |
| Alloy D: | Au | 77.1% by weight |
| | Pt | 7.7% by weight |
| | Pd | 9.5% by weight |
| | Ag | 2.0% by weight |
| | In | 3.5% by weight |
| | Ir | 0.2% by weight. |

Of these alloys, the yield point and the elongation at break were determined in accordance with ISO 6892. Further, stents were manufactured from the alloys examined for their biocompatibility, allergenicity, radiopacity, MRI image and wetting picture. For examining biocompatibility, use was made of the standard EN 10993 from 1996, consideration being given inter alia to cytotoxicity and mutagenicity. The stents according to the invention were found to meet the standard. Wetting was tested by polishing a sample and successively dripping equal amounts of water, physiological saline solution and blood on it. The shape of the drop then gives a picture of the wetting (the flatter the drop, the more wetting, and hence more adhesion of substances).

The MRI image was determined by placing a stent in a plastic vessel filled with a copper sulfate solution suitable for in vitro MR testing. The concentration of copper sulfate was about 1 gram per liter. With a standard 1.5 Tesla MR scanner and gradient echo sequences (Philips ACS-NT), images of the stents were made and examined for signal loss.

The stents of the above alloys according to the invention were compared with commercially available stents for the properties mentioned. The properties of these stents were derived from tables. For Stainless Steel 316 (RVS 316) use was made of the 'Stahlschlüssel', Verlag Stahlschlüssel Wegst GmbH, 1983. The data of Nitinol were derived from 'Das dental Vademecum', Deutsche Ärzte Verlag, no. 5, 1989. The data of tantalum are based on experimental data obtained by doing tensile tests according to ISO 6892. The results are represented in the tables below.

TABLE I data of stents according to the invention

| | Alloy A | Alloy B | Alloy C | Alloy D |
|---|---|---|---|---|
| Yield point (N/mm$^2$) | 560 | 900 | 600 | 600 |
| Elongation at break (%) | 28 | 14 | 18 | 8 |
| Biocompatibility | good | good | good | good |

TABLE I-continued data of stents according to the invention

|  | Alloy A | Alloy B | Alloy C | Alloy D |
|---|---|---|---|---|
| Allergenicity | none | none | none | none |
| Radiopacity | good | good | good | good |
| MRI-image | very good | good | good | good |
| Wetting picture | good | good | good | good |

TABLE II data of commercially available stents

|  | RVS 316* | Nitinol | Tantalum* |
|---|---|---|---|
| Yield point (N/mm²) | approx. 205 | approx. 300 | approx. 200 |
| Elongation at break (%) | approx. 45 | approx. 40 | approx. 35 |
| Biocompatibility | reasonable | reasonable | good |
| Allergenicity | Nickel-containing | Nickel-containing | none |
| Radiopacity | reasonable | moderate | poor |
| MRI-image | poor | reasonable | reasonable |
| Wetting picture | good | moderate | poor |

*Wallstent ®
**Memotherm ®
***Strecker ®

What is claimed is:

1. A stent manufactured from an alloy which contains at least 60% by weight, based on the weight of the alloy, of a combination of gold and palladium, or of a combination of silver and palladium, and the alloy having a yield point of at least 200 N/mm² and an elongation at break of at least 8%.

2. A stent according to claim 1, wherein the weight ratio of gold:palladium is between 3:1 and 0.5:1.

3. A stent according to claim 1, wherein the weight ratio of silver:palladium is between 3:1 and 0.3:1.

4. A stent according to claim 1, wherein the alloy contains at least 0.5% by weight, based on the weight of the alloy, of one or more metals selected from the group consisting of iridium, indium, gallium, tin, titanium, copper, zinc, and ruthenium.

5. A stent according to claim 1, wherein the alloy has a yield point of at least 300 N/mm².

6. A stent according to any claim 1, wherein the alloy has an elongation at break of at least 20%.

7. A stent according to claim 1, wherein the alloy further contains one or more of the metals selected from the group consisting of rhodium, rhenium, cerium, germanium, boron, iron, tantalum, nickel, cobalt, aluminum, niobium, zirconium, manganese, chromium, molybdenum and tungsten.

8. A stent according to claim 1, wherein the alloy further contains one or more elements from the group consisting of silicon and carbon.

* * * * *

UNITED STATES PATENT AND TRADEMARK OFFICE
CERTIFICATE OF CORRECTION

| | | |
|---|---|---|
| PATENT NO. | : 7,087,077 B1 | Page 1 of 1 |
| APPLICATION NO. | : 09/958656 | |
| DATED | : August 8, 2006 | |
| INVENTOR(S) | : Bastiaan Philip Van Dijk et al. | |

It is certified that error appears in the above-identified patent and that said Letters Patent is hereby corrected as shown below:

Title Page;
Please correct the name of the second Inventor listed In the "Inventor" section of the patent, on Page 1, (75) from "Lucas Carolus Van Dijk" to --Lukas Carolus van Dijk--

Signed and Sealed this

Thirty-first Day of March, 2009

JOHN DOLL
*Acting Director of the United States Patent and Trademark Office*